United States Patent [19]

Grollier et al.

[11] Patent Number: 4,656,029
[45] Date of Patent: Apr. 7, 1987

[54] COSMETIC COMPOSITION CONTAINING ALOESIN AS AN AGENT FOR PROTECTION AGAINST SUNLIGHT AND ITS USE FOR SKIN AND HAIR PROTECTION

[75] Inventors: Jean F. Grollier, Paris; Gerard Lang, Saint Gratien; Serge Forestier, Claye-Souilly; Georges Rosenbaum, Asnières, all of France

[73] Assignee: L'Oreal, Paris, France

[21] Appl. No.: 721,424

[22] Filed: Apr. 9, 1985

[30] Foreign Application Priority Data

Apr. 17, 1984 [LU] Luxembourg ............................ 85320

[51] Int. Cl.$^4$ .......................... A61K 7/06; A61K 7/42; A61K 7/44; A61K 7/135
[52] U.S. Cl. ........................................ 424/47; 8/405; 424/DIG. 1; 424/59; 424/60; 424/62; 424/70; 424/71; 424/72; 424/78; 424/81
[58] Field of Search ............................ 424/59, 47, 60

[56] References Cited

U.S. PATENT DOCUMENTS

| 2,338,416 | 1/1944 | Fales | 424/59 |
| 4,154,823 | 5/1979 | Schutt | 514/567 |

FOREIGN PATENT DOCUMENTS

| 52-7062 | 2/1977 | Japan | 424/59 |
| 151113 | 11/1979 | Japan | 424/59 |
| 120621 | 9/1981 | Japan | 424/59 |

OTHER PUBLICATIONS

Gruber et al., Journ. of Pharmaceutical Sciences, 6/1970, vol. 59, No. 6, pp. 830 to 834.
Fairbairn et al., Journ. of Pharmaceutical Sciences, 9/1977, vol. 66, No. 9, pp. 1300 to 1303.
Baber et al., Cosmetics & Toiletries, 10/1981, vol. 96, pp. 67, 68, and 71 to 74.
Meadows, Cosmetics & Toiletries, 11/1980, vol. 95, pp. 51, 52 and 54 to 56.
"Aloe Vera–Eine alte Heilpflanze-neu fur die Kosmetik", vol. 105, No. 17, Oct. 25, 1979.
"C. Glycosyl Compounds, Part VI, Aloesin, a C—Glucosylchromone from Aloe sp.", L. J. Haynes et al., J. of the Chemical Society, pp. 2581-2586, No. 18, C. 1970.
Chem. Abstracts, vol. 67, 1967, p. 9975, 105971d, McCarthy et al.
Chem. Abstracts, vol. 75, 1971, p. 521, 6231w, Holdsworth, Planta Med. 1971, pp. 322-325.
Chemical Abstracts, vol. 78, 1973, p. 4461, 4471n, Holdsworth.
Chemical Abstracts, vol. 87, 1977, p. 262, 164180f, Yagi et al.
"Aloe Vera in Cosmetics", D&Cl, Jun. 1977, Leung et al., pp. 34, 35, 154, 155.
"Natural Sunscreens: Vegetable Derivatives as Sunscreens and Tanning Agents", Proserpio, Cosmetics and Toiletries, vol. 91, 1976, p. 34, 39–42.
"Studies on the Constituents of *Aloe arborescens Mill.* var. *natalensis*", Chem. Pharm. Bull., vol. 21, No. 1, pp. 149-156.
"Studies on the Constituents of *Aloe arborescenis Mill.* var. *natalensis*", Chem. Pharm. Bull., vol. 22, 1974, No. 7, pp. 1565-1590.

*Primary Examiner*—Dale R. Ore
*Attorney, Agent, or Firm*—Cushman, Darby & Cushman

[57] ABSTRACT

The present invention relates to a cosmetic composition containing, as an agent for protecting against light, pure aloesin or an aloe extract containing at least 40% of aloesin and less than 5% of barbaloin, in a quantity of 0.5 to 20% by weight, in a cosmetically acceptable medium.

Such a cosmetic composition can consist of a protective composition, a sunscreen composition or a cosmetic composition stabilized against light and can be applied on skin or to hair.

9 Claims, No Drawings

COSMETIC COMPOSITION CONTAINING ALOESIN AS AN AGENT FOR PROTECTION AGAINST SUNLIGHT AND ITS USE FOR SKIN AND HAIR PROTECTION

The present invention relates to a cosmetic composition containing aloesin and to its use for the protection of skin and hair against sunlight.

It is known that light radiations of wavelengths between 280 and 400 nm permit tanning of human epidermis and that rays of wavelengths between 280 and 320 nm, which are known under the term UV-B produce erythemas and cutaneous burns.

The use of aloe extracts is widespread in the cosmetic field. In particular, it is known to use aloe extracts as well as aloin to prevent solar erythema, this being connected with the ability possessed by these extracts, and to a lesser degree by the aloin subfraction of certain aloe extracts, to absorb solar radiations in the ultraviolet range, in particular in the UV-B range from 280 to 320 nm, which are directly responsible for the appearance of the erythema.

The Aloe genus covers a very wide variety of species. A corollary of this diversity is extreme variability in the composition of aloe extracts. Among the components which may appear in these extracts there may be mentioned:

barbaloin, which is the principal constituent of what is called aloin, which is a subfraction of certain aloe extracts,
aloe-emodin,
homonataloin,
aloenin,
aloesin,
aloesin esters: 2''-0-p-coumaroylaloesin, and 2''-0-feruloylaloesin,
aloinoside,
aloesone.

The screening properties of aloe extracts have been frequently attributed to aloin. In fact, aloesin, which is a major component of certain species of aloe, has excellent properties of absorption in the ultraviolet, and particularly in the UV-B region, with, in particular, an absorption peak at 296 nm, corresponding to a log $\epsilon$ of 3.9.

Now, the Applicant Company has observed that aloe extracts, as well as aloin, which are employed as sunscreens for the protection of the skin and hair, are sensitising, that is to say have an allergenic capability, which is not the case with aloesin.

Moreover, it is well known that aloin is highly sensitive to oxidation, in contrast to aloesin, which makes it necessary to adopt extensive protective measures at the time of the manufacture of the cosmetic composition and during its storage.

The subject of the present invention is therefore a cosmetic composition containing, as an agent for protection against sunlight, and particularly against the UV-B rays, pure aloesin or an extract which is enriched in aloesin and depleted in aloin, and consequently in barbaloin.

Another subject of the invention consists of a process for protection of the skin and hair, natural or sensitised, in respect of solar radiation, employing an effective quantity of such a composition.

By "sensitised hair" there is understood hair which has been subjected to a treatment of permanent waving, colouring or bleaching.

By aloesin-enriched extract there is understood an extract containing at least 40% of aloesin.

By aloin-depleted extract there is understood an extract containing less than 5% of barbaloin.

The cosmetic composition according to the invention consequently contains, as an agent for protection against sunlight, an effective quantity of pure aloesin or of an aloe extract containing at least 40% of aloesin and less than 5% of barbaloin, in a cosmetically acceptable medium.

The cosmetic composition according to the invention contains 0.5 to 20% by weight of aloesin relative to the total weight of the composition and, preferably, 0.5 to 10% by weight of aloesin.

The methods for producing aloe extracts enriched in aloesin are varied and depend substantially on the kind of Aloe employed. In fact, it is necessary to distinguish to Aloe containing aloesin but not barbaloin from the Aloe containing both constituents.

To the first category belong the following species:
Aloe mutabilis
Aloe melanocantha
Aloe manchii
Aloe pearsonii
Aloe comptonii
Aloe mitriformis
Aloe distans
Aloe arenicola
Aloe volkensii
Aloe petrophylla.

Except for the last species mentioned, all the other species contain homonataloin. Insofar as it is possible, attempts will be made to eliminate this homonataloin, which, in point of fact, absorbs in the UV-B ($\lambda_{max}=297$ nm; log $\epsilon=3.85$), but the sensitising action of which is not well known.

To the second category belong the following species:
Aloe ferox
Aloe africana
Aloe globiligemma
Aloe perry
Aloe visckensii
Aloe vera
Aloe lettyae
Aloe capensis
Aloe barbadensis
Aloe socetriis
Aloe curacao
Aloe candelabrum
Aloe excelsa
Aloe cameronii
Aloe sessiliflora
Aloe reitzii
Aloe aculeate
Aloe marlothii
Aloe utyhei densis
Aloe dolomitica
Aloe castanea
Aloe vanlabemii
Aloe alooides
Aloe gerstueri
Aloe petricola.

For the Aloe belonging to the first category, in order to produce an extract it is possible to employ direct aqueous extraction or extraction with acetone or methyl ethyl ketone, followed by evaporation of the solvent.

If the intention is to avoid the presence of homonataloin, it would be essential to employ either acetone or methyl ethyl ketone, cold. Under these conditions, aloesin goes into solution and homonataloin remains in the insoluble residue.

A subsequent purification may be carried out, in the case where the extraction has been carried out using methyl ethyl ketone, by adding water to the organic extract and, after agitation and separation of the aqueous phase by liquid separation, aloesin is recovered in the aqueous phase.

When the aloesin content in the aloe extract obtained is below 40% by weight, the product can then be reconcentrated by a passage over neutral alumina.

To obtain aloe extracts from Aloe belonging to the second category, two types of processes can be envisaged.

The first process consists in collecting aloesin selectively. It is possible to employ the technique of chromatography on a suspension of neutral alumina in 2-propanol, with elution with demineralised water. Barbaloin remains fixed on the column. After filtration of the fraction containing aloesin, in the presence of a cationic resin if appropriate, the aqueous fraction is concentrated by direct evaporation or co-evaporation with methanol.

The second process consists in collecting barbaloin selectively and then recovering an exploitable extract containing a high proportion of aloesin. Among the possible solutions, the following solutions can be envisaged:

The first method starts with an extraction with a methanol/chloroform mixture. After separation, the liquid is evaporated off and the residue taken up with ethyl alcohol. Selective crystallisation of barbaloin takes place in the cold. An aloesin-rich fraction may be recovered by taking the crystallisation liquid in a ketone medium, and then extracting aloesin by treatment of the ketone phase with water, separation and then concentration of the aqueous phase by evaporation.

A second method consists of an initial extraction with acetone or methyl acetate. The residue, after evaporation, is treated with isobutanol. Barbaloin crystallises very quickly. The recrystallisation liquid is taken up in an aqueous medium. After separation, the aqueous phase is concentrated by evaporation.

If the aloesin content is below 40% and the barbaloin content above 5%, the product may be concentrated by passing over neutral alumina.

When the initial extracts contain aloesin esters, it is advantageous, in order to increase the yield of aloesin and to counteract the sensitising action of these products, to carry out a mild hydrolysis of the initial extract, in an acid medium and by subsequently treating the whole mixture.

The present invention is also aimed at an antisolar cosmetic composition containing other agents screening in the ultraviolet, without the content of additional screening agents exceeding 10% of the weight of the composition.

Thus, aloesin or the aloesin-enriched extract, may be combined with other sunscreens specific for the UV-B radiation and/or UV-A radiation, which are compatible with the sunscreen employed according to the invention. It is thus consequently possible to obtain a formulation screening off both UV-B and UV-A radiations.

The compounds according to the invention may be combined with UV-B screens consisting of liposoluble compounds or of oils having screening properties such as, in particular, coffee oil. As lipophilic UV-B sunscreens there may be mentioned salicylic acid derivatives such as 2-ethylhexyl salicylate, homomenthyl salicylate, cinnamic acid derivatives such as 2-ethylhexyl p-methoxycinnamate, 2-ethoxyethyl p-methoxycinnamate, p-aminobenzoic acid derivatives such as amyl p-aminobenzoate and 2-ethylhexyl p-dimethylaminobenzoate, benzophenone derivatives such as 2-hydroxy-4-methoxybenzophenone and 2,2'-dihydroxy-4-methoxybenzophenone, and camphor derivatives such as 3-(4-methylbenzylidene)camphor combined, if appropriate, with 4-isopropyldibenzoylmethane or 3-benzylidenecamphor.

As water-soluble sunscreens screening off the UV-B rays which can also be combined with the screens according to the invention, provided that they are compatible with the latter, mention may be made of the benzylidenecamphor derivatives described in French Patents Nos. 2,199,971, 2,236,515, 2,282,426 and 2,383,904 of the Applicant Company and more particularly 4-(2-oxo-3-bornylidenemethyl)phenyltrimethylammonium methylsulphate, and salts of 4-(2-oxo-3-bornylidenemethyl)benzenesulphonic acid, of 2-methyl-5-(2-oxo-3-bornylidenemethyl)benzenesulphonic acid, and of 2-phenylbenzimidazole-5-sulphonic acid.

The compounds according to the invention may also be combined with UV-A screens among which may be mentioned dibenzoylmethane derivatives.

It will be understood that the list of sunscreens employed in combination with the screens according to the invention which is shown above is not restrictive.

According to a first embodiment of the invention, the cosmetic composition according to the invention is intended to be applied on the skin and can be presented in solution in the form of lotion or oil, in emulsion in the form of cream, pomade, gel or milk, or be packaged as an aerosol and, in general, in any of the usual forms of antiactinic cosmetic compositions.

Among the principal adjuvants which may be present in such a composition, mention may be made of solubilising agents such as water, the lower monoalcohols or polyalcohols containing from 1 to 6 carbon atoms, or an aqueous alcohol solution; it is also possible to mention fatty substances such as mineral, animal or vegetable oils or waxes, fatty acids, fatty acid esters such as triglycerides of fatty acids containing from 6 to 12 carbon atoms, fatty alcohols and oxyethylenated fatty alcohols.

The mono- or polyalcohols which are more particularly preferred are chosen from ethanol, isopropanol, propylene glycol, glycerol, sorbitol and aqueous alcohol mixtures are preferably mixtures of water and ethyl alcohol.

As fatty substances, among mineral oils, vaseline oil can be mentioned; among animal oils, whale, seal, menhaden, halibut liver, cod, tuna, turtle, tallow, neat's foot, horse's hoof, sheep's foot, mink, otter, marmot oil and the like; among vegetable oils, almond, groundnut, wheat germ, olive, corn germ, jojoba, sesame, sunflower, palm, walnut, and similar oils.

Among fatty acid esters, mention may be made of the isopropyl esters of myristic, palmitic and stearic acids and the fatty esters which are solid at 25° C.

It is possible to mention as fatty substances, vaseline, paraffin, lanolin, hydrogenated lanolin, acetylated lanolin and silicone oil.

Among waxes, mention can be made if Sipol wax, lanolin wax, beeswax, candelilla wax, microcrystalline wax, carnauba wax, spermaceti, cocoa butter, karite butter, silicone waxes, hydrogenated oils which are solid at 25° C., sucro-glycerides, and Ca, Mg, Zr and Al oleates, myristates, linoleates and stearates.

Among fatty alcohols mention can be made of lauryl, cetyl, myristyl, stearyl, palmityl and oleyl alcohols, and among polyoxyethylenated fatty alcohols, lauryl, cetyl, stearyl and oleyl alcohols containing from 2 to 20 moles of ethylene oxide.

The cosmetic composition may also incorporate emulsifiers which may be nonionic, anionic, cationic or amphoteric.

It may also be useful to employ thickeners such as cellulose derivatives, polyacrylic acid derivatives, or guar or carob gums.

The cosmetic composition according to the invention may also contain adjuvants usually employed in cosmetics and particularly hydrating products, softeners, colorants, opacifiers, preservatives and perfumes.

It may, if necessary, incorporate an agent for regulating the pH.

The latter is between 4 and 9 but preferably between 5.5 and 8.

In the case of aerosols, conventional propellants will be employed, such as alkanes, fluoroalkanes and chlorofluoroalkanes.

Another subject of the invention consists of the compositions intended to protect natural and sensitised hair against UV rays. These compositions may be presented in the form of shampoos, lotions, gels or emulsions for rinsing to be applied before or after shampooing, before or after dyeing or bleaching, before or after a permanent wave, setting or treating lotions, lotions for blow-drying or for hair setting, hair lacquers, or compositions for permanent waving, dyeing or bleaching hair. These compositions may contain, in addition to the compound of the invention, various adjuvants usually employed in this type of composition, such as surface-active agents, thickeners, polymers, softeners, preservatives, foam stabilizers, electrolytes, organic solvents, silicone derivatives, oils, waxes, anti-fat agents, colorants and/or pigments the function of which is to colour the composition itself or the hair and any other ingredient usually employed in the field of hair-care.

When the compositions consist of shampoos, the latter are substantially characterised by the fact that they contain at least one anionic, nonionic or amphoteric surface-active agent or their mixture and a compound of the invention, in an aqueous medium.

When the compositions consist of non-rinsed lotions—lotions for blow-drying, hair setting lotions, setting or treatment lotions—they incorporate, generally in an aqueous alcoholic or aqueous-alcoholic solution, in addition to the compound of the invention, at least one cationic, ionic, nonionic or amphoteric polymer or their mixture in quantities which are generally between 0.1 and 10% and, preferably, between 0.1 and 3% by weight and, if appropriate, antifoaming agents.

When the compositions consist of rinsed lotions, also called rinses, they are applied before or after bleaching, before or after permanent waving, before or after shampooing or between two shampoo phases, and then rinsed after an application period.

These compositions may be aqueous or aqueous-alcoholic solutions optionally incorporating surfactants, emulsions or gels. These compositions can also be pressurised as an aerosol.

Another subject of the invention is a cosmetic composition whose UV ray-sensitive components are protected against light radiations by the presence of pure aloesin or an aloesin-enriched aloe extract, the quantity of pure aloesin varying between 0.5 and 10% by weight; these compositions, containing one or more compounds which are particularly sensitive to ultraviolet rays, can form hair-care compositions such as hair lacquers, hair setting lotions which are coloured or uncoloured, shampoos, colouring shampoos, hair-dyeing compositions, makeup products, skin-treatment creams and, in general, any cosmetic composition which is capable of presenting stability problems when stored in light because of its components.

The following examples illustrate the invention without, however, restricting it.

EXAMPLE 1

| EMULSION FOR SKIN | | |
|---|---|---|
| Purified aloesin | | 3.0 g |
| Sipol wax | | 7.0 g |
| Glycerol monostearate | | 2.0 g |
| Vaseline oil | | 15.0 g |
| Silicone oil | | 1.5 g |
| Cetyl alcohol | | 1.5 g |
| Glycerine | | 10.0 g |
| Perfume | q.s. | |
| Preservative(s) | q.s. | |
| Colorant(s) | q.s. | |
| Water | q.s. | 100 g |

The emulsion is prepared in a conventional manner by heating the fatty substances and the emulsifiers to 80°85° C. The aqueous phase containing aloesin is heated to the same temperature and the fatty phase is added to the aqueous phase with vigorous stirring. After 15 minutes' vigorous stirring the mixture is allowed to cool with moderate stirring.

EXAMPLE 2

| EMULSION FOR SKIN | | |
|---|---|---|
| Debarbaloinated aloe extract containing at least 70% of aloesin | | 8.0 g |
| Stearic acid | | 2.0 g |
| Cetyl alcohol | | 1.2 g |
| Self-emulsifiable glycerol monostearate | | 6.0 g |
| Sorbitan monostearate polyoxyethylenated with 60 moles of ethylene oxide | | 2.0 g |
| Lanolin | | 4.0 g |
| Vaseline oil | | 30.0 g |
| Triethanolamine | | 0.1 g |
| Perfume | q.s. | |
| Preservative(s) | q.s. | |
| Colorant(s) | q.s. | |
| Water | q.s. | 100 g |

This emulsion is prepared in the same manner as in Example 1

EXAMPLE 3

| EMULSION FOR SKIN | |
|---|---|
| Purified aloesin | 2.0 g |
| 3-Benzylidenecamphor | 2.0 g |
| Vaseline oil | 10.0 g |
| Sunflower oil | 5.0 g |
| Polyoxyethylenated hydrogenated palm oil | 5.0 g |

-continued

| EMULSION FOR SKIN | | |
|---|---|---|
| Cetylstearyl alcohol with 15 moles of ethylene oxide | | 5.0 g |
| Lanolin | | 3.0 g |
| Propylene glycol | | 5.0 g |
| Perfume | q.s. | |
| Preservative(s) | q.s. | |
| Colorant(s) | q.s. | |
| Water | q.s. | 100 g |

This emulsion is prepared in the same manner as in Example 1 by adding 3-benzylidenecamphor in the fatty phase.

EXAMPLE 4

| EMULSION FOR SKIN | | |
|---|---|---|
| Purified aloesin | | 2 g |
| 4-[(2-Oxo-3-bornylidene)methyl]phenyltrimethylammonium methylsulphate | | 3 g |
| 4-Isopropyldibenzoylmethane | | 1.5 g |
| Sorbitan stearate | | 3.0 g |
| Sorbitan stearate with 20 moles of ethylene oxide | | 4.0 g |
| Preservative | | 0.5 g |
| Perfume | q.s. | |
| Water | q.s. | 100 g |

The preparation of the emulsion is similar to that in Example 3, except that in this case 4-[(2-oxo-3-bornylidene)]methyl(sic)phenyltrimethylammonium methylsulphate is dissolved in the aqueous phase, 4-isopropyldibenzoylmethane being dissolved in the fatty phase.

EXAMPLE 5

The following shampoo is prepared:

| | | |
|---|---|---|
| Sodium lauryl ether sulphate with 2 moles of ethylene oxide sold at a concentration of 25% of active substance (AS) | | 5 g AS |
| C$_{12-18}$—alkyldimethylcarboxymethylammonium hydroxide containing 30% AS sold under the name "Dehyton AB 30" by Henkel | | 3 g AS |
| Aloesin | | 1 g AS |
| NaOH | q.s. | pH 5 |
| Water | q.s. | 100 g |

EXAMPLE 6

The following non-rinsed lotion is prepared:

| | | |
|---|---|---|
| Aloesin | | 1.5 g AS |
| Polyvinylpyrrolidone | | 0.75 g AS |
| NaOH | q.s. | pH 8.5 |
| Ethyl alcohol/water 50/50 | q.s. | 100 g |

The compositions of Examples 5 and 6 are applied to hair to protect it from UV rays.

We claim:

1. A cosmetic sunscreening composition for protecting hair and skin against sunlight, which comprises an effective UV-B absorbing quantity of pure aloesin or of an aloe extract containing at least 40% of aloesin and less than 5% of barbaloin, in a cosmetically acceptable medium, wherein pure aloesin or aloe extract filters out the UV-B rays of wavelengths between 280 and 320 nm.

2. The cosmetic composition of claim 1 which comprises 0.5 to 20% by weight of aloesin relative to the total weight of the composition.

3. The cosmetic composition of claim 2 which comprises 0.5 to 10% by weight of aloesin relative to the total weight of the composition.

4. The cosmetic composition of claim 1, intended to be applied on the skin in the form of a lotion, oil, cream, pomade, gel, milk or aerosol, which comprises at least one cosmetic adjuvant selected from the group consisting of water, a lower mono-alcohol or poly-alcohol containing from 1 to 6 carbon atoms, a mixture of water with said alcohol, mineral, animal or vegetable oil or wax, a fatty acid, a fatty acid ester, a fatty alcohol, an oxyethylenated fatty alcohol, an emulsifier, a thickener, a hydrating product, a softening product, a colorant, an opacifier, a preservative, a perfume, a pH-regulating agent and a propellant.

5. The cosmetic composition of claim 4 which has a pH between 4 and 9.

6. The cosmetic composition of claim 4 which has a pH between 5.5 and 8.

7. The cosmetic composition of claim 1 which further comprises up to 10% by weight of a sunscreen agent different from said aloesin or aloe extract and selected from the group consisting of coffee oil, salicyclic acid derivative, cinnamic acid derivative, p-aminobenzoic acid derivative, benzophenone derivative, 3-benzylidene camphor, 3-(4-methyl benzylidene)camphor and dibenzoylmethane derivative.

8. A cosmetic composition comprising one or more UV ray-sensitive components, which is protected against light radiations by the presence of 0.5 to 10% by weight of pure aloesin.

9. A process for protecting skin and hair against sunlight which comprises applying to the skin or hair an effective quantity of a cosmetic sunscreening composition according to claim 1.

* * * * *